United States Patent [19]

Yetman

[11] Patent Number: 4,919,784
[45] Date of Patent: Apr. 24, 1990

[54] ELECTROPHORRESIS CASSETTE SPACER
[75] Inventor: David S. Yetman, Merrimack, Mass.
[73] Assignee: EG&G, Inc., Wellesley, Mass.
[21] Appl. No.: 394,554
[22] Filed: - Aug. 16, 1989
[51] Int. Cl.5 ................... G01N 27/28; G01N 27/26; B01D 57/02
[52] U.S. Cl. ............................ 204/299 R; 204/182.8
[58] Field of Search ............. 204/299 R, 182.8, 180.1
[56] References Cited

U.S. PATENT DOCUMENTS

| | | | |
|---|---|---|---|
| 3,980,540 | 9/1976 | Hoefer | 204/299 R X |
| 4,224,134 | 9/1980 | Hoefer et al. | 204/299 R |
| 4,325,796 | 4/1982 | Hoefer et al. | 204/299 R X |
| 4,339,327 | 7/1982 | Tyler | 204/299 R |
| 4,560,459 | 12/1985 | Hoefer | 204/299 R X |
| 4,576,693 | 3/1986 | Kreisher et al. | 204/299 R X |
| 4,663,015 | 5/1987 | Sleeter et al. | 204/299 R |

Primary Examiner—John F. Niebling
Assistant Examiner—John S. Starsiak, Jr.
Attorney, Agent, or Firm—Wolf, Greenfield & Sacks

[57] ABSTRACT

A spacer for an electrophoresis cassette of the type having front and rear plates, such as glass, with a gel material in the space between the plates in which electrophoresis separation is performed. The cassette includes a spacer between the plates in the form of a thin disk whose thickness is equal to the desired plate separation. A stud projects outwardly from the disk and is received in a hole in one of the plates to locate the stud. Preferably the stud is made of stainless steel.

12 Claims, 1 Drawing Sheet

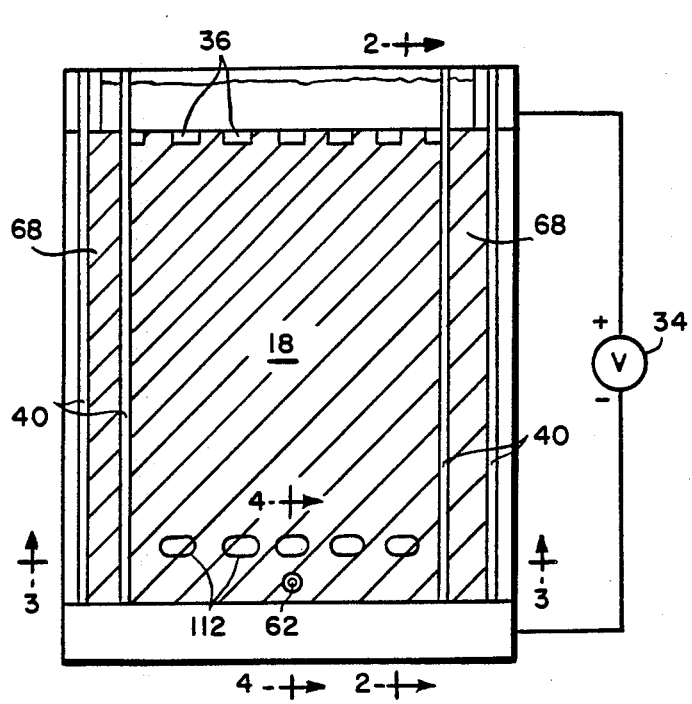
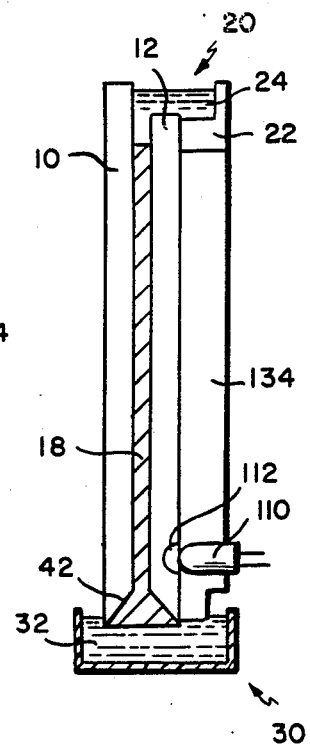
FIG. 1
FIG. 2
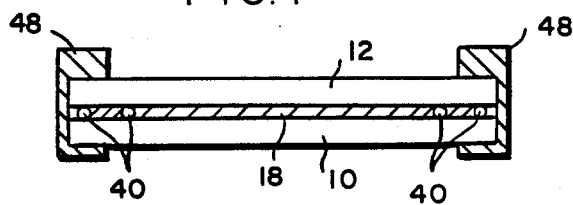
FIG. 3
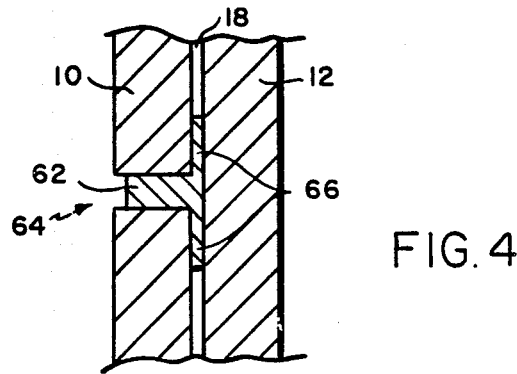
FIG. 4

ELECTROPHORRESIS CASSETTE SPACER

FIELD OF THE INVENTION

The present invention is related to electrophoresis systems, and in particular to a spacer for use with an electrophoresis cassette.

BACKGROUND OF THE INVENTION

Proteins and other large bioloqical molecules, includinq DNA, may be separated for analysis using electrophoresis techniques. One particularly important application of these techniques is the sequencinq of the DNA and RNA molecules. In performinq an electrophoresis separation of such molecules, a gel is formed between two non-conducting plates, such as glass, to form a thin sheet of gel between the glass surfaces.

The collection of molecules to be sorted is placed at the negative electrode end of the gel, usually in preformed wells. The molecules are negatively charqed, and the electric field in the qel reacts with the charge on the molecules to provide a force propelling the molecules through the gel towards the positive electrode. Smaller molecules have less resistance to traveling through the gel than larger molecules, resulting in a separation and sorting of the molecules by size as they migrate throuqh the gel.

Synthesis of fractional lengths of DNA (or RNA) molecules by means of enzymes allows the molecule to be analyzed according to the sequence of bases making up such a molecule. Techniques for doing this type of analysis are well known. See for example Sanger. F., S. Nicklen & A.R. Coulson 1977 Proc. Natl. Acad. Sci. USA 74: 5463–5467; Prescott L. Deininger Analytical Biochemistry 135, 247–263 (1983); Garoff, H., & Ansorge, W. (1981) Anal. Biochem. 115, 450–457; and Biggin, M. D., T. J. Gibson & A. F. Hong 1983 Proc. Natl. Acad. Sci. USA 80: 3963-3965.

It is important to the proper functioning of the electrophoresis process that the gel be uniform in thickness and other property in the region where the separation is performed. Non-uniformities in the thickness of the gel result in perturbations of the electric field which will adversely affect the accuracy of the electrophoresis separation. The present invention is directed toward maintaining uniform qel thickness in an electrophoresis cassette.

SUMMARY OF THE INVENTION

Briefly, the present invention includes an improvement to electrophoresis cassettes which provides added uniformity to the thickness of the gel layer inside the cassette. The improvement consists of the addition of a spacer between the front and back plates of the cassette. Preferably, the spacer is made of stainless steel and is retained in place by means of a stud which extends into a corresponding hole in one of the plates of the electrophoresis cassette.

DESCRIPTION OF THE DRAWINGS

The advantages and operation of the present invention will become more clear upon the reading the following description of the preferred embodiment in conjunction with the accompanying drawings of which:

FIG. 1 is a front view of a cassette incorporating the invention;

FIG. 2 is a side view of a cassette incorporating the invention;

FIG. 3 shows a horizontal section through the cassette of FIG. 1; and

FIG. 4 shows further details of the spacer used in the cassette of FIGS. 1-3.

DESCRIPTION OF THE PREFERRED EMBODIMENT

Referring to FIGS. 1-3, there is shown a typical qel cell or cassette used for electrophoresis separation of DNA and RNA molecule fragments. Two flat plates 10 and 12 are brought together facing one another and separated by side spacers 14 and 16. The front and back plates should be madg of a flat, non-porous insulator which does not react with the qel material or the molecules being analyzed. Typically. plates 10 and 12 are formed of glass. Front and back plates are typical on the order of 8 inches by 12 inches.

Spacers 40 are placed between the front and back plates 10 and 12 to provide a uniform qap between the plates into which the gel is placed. The spacers determine the qel thickness and are on the order of 0.010 to 0.020 inches thick. In the preferred embodiment, two monofilament spacers 40 are provided on each side of the qel layer 18. Front and back plates 10 and 12 are spaced apart from one another by means of the spacers 40 which provide a line contact between each of the spacers and the front and back plates 10 and 12. Other types of spacers may be used, such as flat spacers or single strands of monofilament.

To form the gel layer, the components in FIG. 1 are brought together as described above. The front and back glass plates 10 and 12 are held apart by the side spacers 40. The edges of front and back plates 10 and 12 are clamped together so that the qel material which will be inserted between the plates cannot escape through the sides. Side clamps 48 are used to hold the front and back plates 10 and 12 in contact with spacers 40. These clamps run the entire length of the gel cell from the bottom to the top of plates 10 and 12. The location of clamps 48 is illustrated in FIG. 3. The gel is then formed between front and glass plates.

A suitable material such a polyacrylamide or agarose gel is used to fill the space between plates 10 and 12. These materials are liquid when they are poured or injected between the plates, after which the materials solidify to form a gel. It is important for the proper operation of the electrophoresis separation that the gel be as uniform as possible. Any imperfection in the gel will affect the speed and direction in of the molecule's diffusion under the influence of the electric field applied to the qel. Imperfections may be caused by air bubbles or dust within the gel and by other factors, as discussed below.

Further information on the construction of a cassette as shown in FIGS. 1-3 is found in co-pendinq application, Ser. No. 127,655, and also in published U.K application number 2,206,696A.

A reservoir 20 containinq a buffer solution 24 is formed at the top of the cassette to provide an electrical connection to the top of the qel material 18. Typically, the reservoir is formed between an upper extension 26 of the front glass plate 10 and a rear piece 22 which forms the floor and sides of the rear of the reservoir.

The bottom of the gel cassette is immersed in a bottom reservoir 30 containing a second buffer solution 32 which provides electrical contact with the bottom of the gel layer 18. A voltage source 34 is electrically connected between the top buffer solution 24 and the bottom buffer solution 32. Typically, the voltage from voltage source 34 is on the order of 1000 volts. The electric potential between the top and bottom buffer solutions induces an electric field within the qel layer 18. The objective is to provide a completely uniform electric field within the qel layer 18 having equipotential lines which are exactly parallel to the horizontal extent of the qel layer.

Normally, electrophoresis of several collections of molecules are run through the gel at the same time. In FIG. 1, a plurality of wells 36 is formed in the top of the qel layer 18. A collection of molecules to be separated is injected into each of the wells by means of a hypodermic needle small enough to fit in the narrow opening between the front and back plates 10 and 12 of the gel cassette.

Wells 36 may be formed by means of a piece of thin plastic, equal in thickness to side spacers 40 which is cut in the proper shape to form the well configuration shown in FIG. 2. This piece is called a "comb." The comb is inserted after the liquid qel solution has been poured and before the gel hardens. Other well configurations may be used. After the gel has hardened, the comb is removed to leave the wells in which the molecules to be analyzed are placed.

The electrophoresis system may include addition apparatus to automatically detect molecules diffusing through the gel. For example, detectors for responding to radiation from radio-labelled molecule segments may be used to automatically detect the passage of such molecule segments.

In FIGS. 1 and 2, a plurality of detectors 11 are located behind the lower portion of the qel cell. These may be mounted, for example, in a back plate 134 which supports the cassette during electrophoresis separation runs. Each detector receives radiation emerging through an associated collimator 112 in the rear glass plate 12. As the radio-labelled molecule fragments travel downwardly from each of the wells 36 under the influence of the electric field, they will pass the corresponding collimator 112 and detector 110 at a time determined by the molecule size and resulting diffusion speed. By electronically detecting the passage of these molecular fragments an automatic analysis of the material may be performed.

The accuracy with which the electrophoresis separation is performed depends upon maintaining a uniform electric field within the gel layer. One of the factors influencing the uniformity of the electric field is the thickness of the qel layer between the glass plates. It has been found that in assembling cassettes of the type shown in FIGS. 1-3, the bottom portions of the plates 10 tend to bow in toward each other by a slight amount as the gel solidifies. The reason for this is not known. This effect is more pronounced at the bottom portion of the gel layer than at the top, possibly because the comb used to form wells 36 serves to maintain the desired spacing between the front and back plates at the top of the electrophoresis cassette.

It has been found that a small spacer 64 may be placed between the front and back plates 10 and 12 at the bottom of the cassette without adversely affecting the operation of the cassette. The configuration and placement of the spacer is shown in more detail in FIG. 4. In FIG. 4, spacer 64 includes a disk shaped portion 66 whose thickness is equal to the desired spacing between the plates. Typically, this is on the order of 0.010" to 0.020". The spacer is maintained in place by means of a protuberance, such as stud 62, which extends outwardly from disk portion 66. In FIG. 4, stud 62 extends into a hole which has been drilled completely through the front plate 10.

The diameter of disk portion 66 is approximately ⅛ inch, and the diameter of the stud portion 62 is 0.060 inches in the described embodiment. While the hole in which the stud is retained is shown in FIG. 4 as going completely through glass plate 10, the hole may alternately be formed so as to only go partially through the glass plate. Spacer 64 may be located by inserting its stud 62 into a hole in either the front glass plate 10 or the rear glass plate 12.

The preferred material for spacer 64 is stainless steel. The spacer 64 is located below the level of or "downstream" (with reference to the direction of travel of molecules to be separated) from detectors 110. This typically reduces any perturbations which might be introduced by the metallic spacer in the electric field in the area above the detectors to a small enough level to produce negligible errors in the electrophoretic separation process. While the use of plastic, or other non-conductive materials might further reduce the effect of the spacer on the electric field, it is difficult to keep the tolerance of such a spacer within acceptable limits. In particular, the thickness of the disk portion 66 of spacer 54 should be within 0.0005 inches of the desired dimension, and preferably the tolerance should be 0.0001 inches or less. It is difficult to fabricate plastic spacers to such tolerances, and thus the use of stainless steel or a similar material is preferred.

The spacer is preferably retained within its hole by means of an adhesive. Due to the large difference in temperature coefficient between the glass plate and the spacer material, it is hard to obtain a press fit for spacer 64. The temperature of the cassette will increase markedly due to the power dissipated by the electrophoresis process, and the resulting temperature increase exacerbates the problems caused by differential expansion. Retaining spacer 64 by means of a press fit results in a significant risk that the glass plate may crack with changes in temperature. The preferred adhesive is a silicone elastomeric adhesive, such as Dow Corning 118-RTV. The adhesive is placed both behind disk portion 66 and around stud portion 62 of the spacer.

More than one spacer 64 may be used in a single cassette. Where a very wide cassette is used to concurrently perform a large number of separations, multiple spacers across the width of the cassette may be required. In such circumstances, spacers may also be required in the area above the level of detectors 110. In this case, plastic spacers are preferably used in the area upstream of the detectors, rather than metallic spacers, in order to minimize the effects of the spacer on the electric field in the gel.

There has been described a new spacer for use with a gel cassette and for performing an automated electrophoresis diffusion which has advantages over methods and devices previously used. It should be apparent that modifications to the preferred embodiment disclosed herein above will be made by those of ordinary skill when using the teachings of the present invention in different applications and situations. Accordingly, the invention should not be deemed to be limited by the particular embodiments utilized above to explain the features of the invention. Rather, the invention should only be interpreted in accordance with the following claims.

What is claimed is:

1. An electrophoresis cassette, comprising:
 a first flat plate having two sides which are substantially parallel to each other and having top and bottom edges;
 a second flat plate having two sides which are substantially parallel to each other and having top and bottom edges;
 means for holding the first and second plate in a fixed relationship with each other wherein the sides of the first plate are substantially parallel to the sides of the second plate and the opposing faces of the plates are separated by a predetermined distance to form a space therebetween, the sides, bottom edges and top edges of the plates corresponding to the sides, bottom edge and top edge of the assembled cassette;
 the space between the plates being adapted for filling with a qel in which an electrophoresis separation may be performed;
 the means for holding including means for providing a seal between the first and second plates along each of the sides of the cassette;
 at least one spacer located between the first and second plates and between the seals along each of the cassette sides and including a flat portion, the thickness of which is equal to the predetermined distance between the plates, and a protrusion which extends from the flat portion;
 one of the front and back plates including an opening on the inside surface thereof for receiving the protrusion to maintain the spacer in a fixed position.

2. The apparatus of claim 1 wherein the opening includes a cylindrical hole going throuqh the plate, and wherein the protrusion is a cylindrical stud having a diameter substantially equal to the diameter of the cylindrical hole.

3. The apparatus of claim 2 wherein the flat portion is in the shape of a disk.

4. The apparatus of claim 1 wherein the cassette includes means for detecting materials being electrophoretically separated in the cassette as they pass a datum line extending laterally across the cassette substantially perpendicular to the sides of the cassette; and
 wherein the spacer is located downstream of the datum line so that said materials have passed the datum line before passing the spacer.

5. The apparatus of claim 4 wherein the means for detection includes a plurality of detectors located along the datum line.

6. The apparatus of any of claims 1-4 wherein the spacer is formed of metal.

7. The apparatus of any of claims 1-4 wherein the spacer is formed of stainless steel.

8. The apparatus of any of claims 1-3 wherein the thickness of the flat portion of the spacer is between 0.010" and 0.020 inches.

9. The apparatus of claim 6 wherein the spacer is maintained in place by means of an adhesive material.

10. The apparatus of claim 9 wherein the adhesive is a silicone elastomer.

11. The apparatus of claim 4 wherein the spacer is located at least one inch below the datum line.

12. The apparatus of claim 1-3 wherein the means for providing a seal includes on each side of the space between the plates at least one piece of monofilament located between the two plates and substantially parallel to the sides of the plates to provide a line contact seal between the monofilament and each plate.

* * * * *

UNITED STATES PATENT AND TRADEMARK OFFICE
CERTIFICATE OF CORRECTION

PATENT NO. : 4,919,784                    Page 1 of 2

DATED : April 24, 1990

INVENTOR(S) : David S. Yetman

It is certified that error appears in the above-identified patent and that said Letters Patent is hereby corrected as shown below:

In the title on the cover page and in Column 1, "Electrophorresis" should read as --Electrophoresis--.

Column 1, line 11 change "bioloqical" to --biological--.
Column 1, line 14 change "sequencinq" to --sequencing--.
Column 1, line 15 change "performinq" to --performing--.
Column 1, line 21 change "charqed" to --charged--.
Column 1, line 22 change "qel" to --gel--.
Column 1, line 28 change "throuqh" to --through--.
Column 1, line 48 change "qel" to --gel--.
Column 2, line 10 change "qel" to --gel--.
Column 2, line 15 change "madg" to --made--.
Column 2, line 16 change "qel" to --gel--.
Column 2, line 21 change "qap" to --gap--.
Column 2, line 23 change "qel" to --gel--.
Column 2, line 36 change "qel" to --gel--.
Column 2, line 51 change "molecule's" to --molecules'--.
Column 2, line 54 change "qel" to --gel--.
Column 2, line 58 change "U.K" to --U.K.--.
Column 2, line 60 change "containinq" to --containing--.
Column 2, line 62 change "qel" to --gel--.
Column 3, line 3 change "voltaqe" to --voltage--.

UNITED STATES PATENT AND TRADEMARK OFFICE
CERTIFICATE OF CORRECTION

PATENT NO. : 4,919,784

DATED : April 24, 1990

INVENTOR(S) : David S. Yetman

It is certified that error appears in the above-identified patent and that said Letters Patent is hereby corrected as shown below:

```
Column 3, line  6 change "qel" to --gel--.
Column 3, line  8 change "qel" to --gel--.
Column 3, line 10 change "qel" to --gel--.
Column 3, line 14 change "qel" to --gel--.
Column 3, line 23 change "qel" to --gel--.
Column 3, line 34 change "11" to --110--.
Column 3, line 35 change "qel" to --gel--.
Column 3, line 52 change "qel" to --gel--.
In Claim 1, Column 5, line 21 change "qel" to --gel--.
In Claim 2, Column 5, line 36 change "throuqh" to --through--.
```

Signed and Sealed this

Twenty-seventh Day of August, 1991

Attest:

Attesting Officer

HARRY F. MANBECK, JR.

Commissioner of Patents and Trademarks